United States Patent
Suga et al.

(10) Patent No.: US 8,436,210 B2
(45) Date of Patent: May 7, 2013

(54) AMIDE COMPOUND AND BACTERIAL DISEASE CONTROL AGENT FOR AGRICULTURAL AND HORTICULTURAL USE

(75) Inventors: Hiroaki Suga, Tokyo (JP); Jun Igarashi, Tokushima (JP)

(73) Assignees: The University of Tokyo, Tokyo (JP); Otsuka Chemical Co., Ltd., Osaka-shi (JP)

(*) Notice: Subject to any disclaimer, the term of this patent is extended or adjusted under 35 U.S.C. 154(b) by 222 days.

(21) Appl. No.: 12/740,064

(22) PCT Filed: Nov. 6, 2008

(86) PCT No.: PCT/JP2008/070166
§ 371 (c)(1),
(2), (4) Date: Apr. 27, 2010

(87) PCT Pub. No.: WO2009/060882
PCT Pub. Date: May 14, 2009

(65) Prior Publication Data
US 2010/0261920 A1    Oct. 14, 2010

(30) Foreign Application Priority Data
Nov. 9, 2007  (JP) .................................. 2007-291658

(51) Int. Cl.
*C07C 233/31* (2006.01)
*C07C 235/14* (2006.01)
*C07C 211/00* (2006.01)

(52) U.S. Cl.
USPC ............. 564/217; 564/462; 564/65; 564/199; 568/347; 554/36; 554/65

(58) Field of Classification Search ........................ None
See application file for complete search history.

(56) References Cited

U.S. PATENT DOCUMENTS
2004/0115732 A1    6/2004  Suga

FOREIGN PATENT DOCUMENTS
JP    2006-512290 A1    4/2006

OTHER PUBLICATIONS

T. Kato, et al.; "Studies on Ketene and Its Derivatives. XLIII. Reaction of Primary Enamines with Ketene and Diketene;" Journal of the Pharmaceutical Society of Japan; vol. 91; No. 7; Jul. 1971; pp. 740-749 and Cover Sheet (11 Sheets.).
International Search Report for International Application No. PCT/JP2008/070166 dated Jan. 23, 2009.

*Primary Examiner* — Yate K Cutliff
(74) *Attorney, Agent, or Firm* — Kratz, Quintos & Hanson, LLP

(57) ABSTRACT

The present invention provides an amide compound having antibacterial activity, and a bacterial infection control agent for agricultural and horticultural use that contains the amide compound. The novel amide compound of the present invention is represented by General Formula (1):

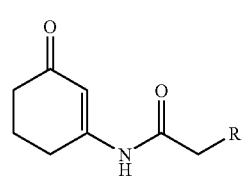

Figure 1:
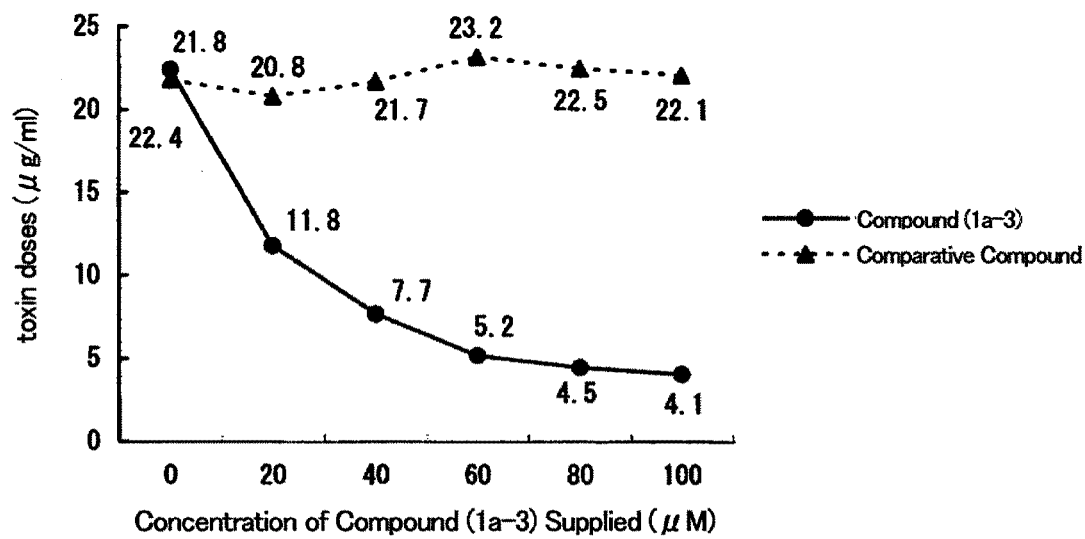

wherein R is a —CH($R^1$)($R^2$) or a —CO($R^2$) group, $R^1$ is a hydrogen atom or a hydroxyl group, and $R^2$ is a $C_{1-12}$ alkyl group.

9 Claims, 2 Drawing Sheets

AMIDE COMPOUND AND BACTERIAL DISEASE CONTROL AGENT FOR AGRICULTURAL AND HORTICULTURAL USE

TECHNICAL FIELD

The present invention relates to an amide compound and a bacterial infection control agent for agricultural and horticultural use.

BACKGROUND ART

Bacterial plant infections are known to be intractable. Most common, commercially available agents that are effective for treating plant infections caused by fungi (filamentous fungi) are not effective for treating bacterial infections; therefore, only a limited number of agents, such as inorganic or organic copper fungicides, streptomycin, oxolinic acids, and biological pesticides, are currently used as bacterial infection control agents. Furthermore, even when these control agents are used, a satisfactory control effect cannot always be achieved depending on the type of farm product. In recent years, the generation of oxolinic-acid-resistant *Burkholderia glumae* and the like has been reported. This makes the control of bacterial plant infections even more difficult.

Patent Document 1 discloses that some types of amide compounds act on bacteria to inhibit biofilm (biomembrane) formation. However, the document is silent about the control effect of the amide compound on bacterial plant infections. In fact, as is clear from the Test Example described later, the amide compound of Patent Document 1 has no control effect on bacterial infections.

Under the current situation in which there is an insufficient variety of agents that are effective for controlling bacterial plant infections, there is a strong demand for the development of such agents.

Patent Document 1: Japanese Unexamined Patent Publication No. 2006-512290

DISCLOSURE OF THE INVENTION

Problem to be Solved by the Invention

An object of the present invention is to provide a compound that is extremely effective for controlling bacterial infections.

Means for Solving the Problem

The present inventors have been conducting extensive research to achieve the above object. As a result, they found that a compound having a certain amide structure exhibits antibacterial activity, more specifically suppresses toxin production from bacteria, thereby enabling the object of the present invention to be achieved. The present invention has been accomplished based on these findings.

The present invention provides an amide compound and a bacterial infection control agent for agricultural and horticultural use comprising the amide compound as shown in Items 1-9 below.

Item 1. An amide compound represented by General Formula (1):

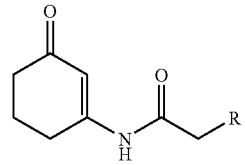

(1)

wherein R is a —CH($R^1$)($R^2$) or a —CO($R^2$) group, $R^1$ is a hydrogen atom or a hydroxyl group, and $R^2$ is a $C_{1-12}$ alkyl group.

Item 2. The amide compound according to Item 1, wherein R is a —CH($R^1$)($R^2$) group, $R^1$ is a hydrogen atom, and $R^2$ is a $C_{2-10}$ alkyl group in General Formula (1).

Item 3. The amide compound according to Item 1, wherein R is a —CH($R^1$)($R^2$) group, $R^1$ is a hydrogen atom, and $R^2$ is a $C_{4-8}$ alkyl group in General Formula (1).

Item 4. The amide compound according to Item 1, wherein R is a —CH($R^1$)($R^2$) group, $R^1$ is a hydrogen atom, and $R^2$ is an n-hexyl group in General Formula (1).

Item 5. A bacterial infection control agent for agricultural and horticultural use, comprising an amide compound represented by General Formula (1):

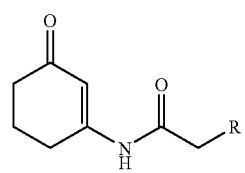

(1)

wherein R is a —CH($R^1$)($R^2$) or a —CO($R^2$) group, $R^1$ is a hydrogen atom or a hydroxyl group, and $R^2$ is a $C_{1-12}$ alkyl group.

Item 6. The control agent comprising an amide compound according to Item 5, wherein R is a —CH($R^1$)($R^2$) group, $R^1$ is a hydrogen atom, and $R^2$ is a $C_{2-10}$ alkyl group in General Formula (1).

Item 7. The control agent comprising an amide compound according to Item 5, wherein R is a —CH($R^1$)($R^2$) group, $R^1$ is a hydrogen atom, and $R^2$ is a $C_{4-8}$ alkyl group in General Formula (1).

Item 8. The control agent comprising an amide compound according to Item 5, wherein R is a —CH($R^1$)($R^2$) group, $R^1$ is a hydrogen atom, and $R^2$ is an n-hexyl group in General Formula (1).

Item 9. The bacterial infection control agent for agricultural and horticultural use according to any one of Items 5 to 8, wherein the bacterial infection is *Burkholderia* infection.

The amide compound of the present invention is represented by General Formula (1):

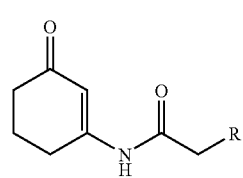

(1)

wherein R is a —CH(R¹) or a —CO(R²) group, R¹ is a hydrogen atom or a hydroxyl group, and R² is a $O_{1-12}$ alkyl group.

Examples of $C_{4-8}$ alkyl groups, $C_{2-10}$ alkyl groups, and $C_{1-12}$ alkyl groups of the present invention are as follows.

Examples of $C_{4-8}$ alkyl groups include $C_{4-8}$ straight- or branched-chain alkyl groups such as n-butyl, isobutyl, sec-butyl, tert-butyl, n-pentyl, 1-methyl-n-butyl, 2-methyl-n-butyl, 3-methyl-n-butyl, 1,1-dimethyl-n-propyl, 1,2-dimethyl-n-propyl, 2,2-dimethyl-n-propyl, 1-ethyl-n-propyl, n-hexyl, 1-methyl-n-pentyl, 2-methyl-n-pentyl, 3-methyl-n-pentyl, 4-methyl-n-pentyl, 1,1-dimethyl-n-butyl, 1,2-dimethyl-n-butyl, 1,3-dimethyl-n-butyl, 2,2-dimethyl-n-butyl, 2,3-dimethyl-n-butyl, 3,3-dimethyl-n-butyl, 1-ethyl-n-butyl, 2-ethyl-n-butyl, 1,1,2-trimethyl-n-propyl, 1,2,2-trimethyl-n-propyl, 1-ethyl-1-methyl-n-propyl, 1-ethyl-2-methyl-n-propyl, 1-methyl-1-ethyl-n-pentyl, n-heptyl, 2-heptyl, 1-ethyl-1,2-dimethyl-n-propyl, 1-ethyl-2,2-dimethyl-n-propyl, n-octyl, 3-octyl, 4-methyl-3-n-heptyl, 6-methyl-2-n-heptyl, 2-propyl-1-n-heptyl, and 2,4,4-trimethyl-1-n-pentyl.

Examples of $C_{2-10}$ alkyl groups include, in addition to the above-mentioned $C_{4-8}$ alkyl groups, $O_{2-10}$ straight- or branched-chain alkyl groups such as ethyl, n-propyl, isopropyl, n-nonyl, 2-nonyl, 2,6-dimethyl-4-n-heptyl, 3-ethyl-2,2-dimethyl-3-n-pentyl, 3,5,5-trimethyl-1-n-hexyl, n-decyl, 2-decyl, 4-decyl, 3,7-dimethyl-1-n-octyl, and 3,7-dimethyl-3-n-octyl.

Examples of $C_{1-12}$ alkyl groups include, in addition to the above-mentioned $C_{2-10}$alkyl groups, $C_{1-12}$ straight- or branched-chain alkyl groups such as methyl, n-undecyl, 2-undecyl, n-dodecyl, and n-tridecyl.

The amide compounds of the present invention represented by General Formula (1) include the amide compounds represented by General Formulae (1a) and (1b) below:

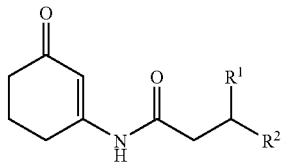

(1a)

wherein R¹ and R² are the same as above; and

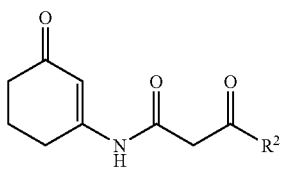

(1b)

wherein R² is the same as above.

Among the amide compounds represented by General Formulae (1a) and (1b), the amide compounds represented by General Formula (1a) are preferable from the viewpoint of their control effect.

Among the amide compounds represented by General Formula (1a), an amide compound wherein R¹ is a hydrogen atom is preferable. Among the amide compounds represented by General Formula (1a), an amide compound wherein R² is a $C_{2-10}$alkyl group is preferable. More preferably, R² is a $C_{4-8}$ alkyl group, and still more preferably, R² is an n-hexyl group.

The amide compound of the present invention represented by General Formula (1) above can be prepared by the process, for example, shown in Reaction Formula 1 or Reaction Formula 2.

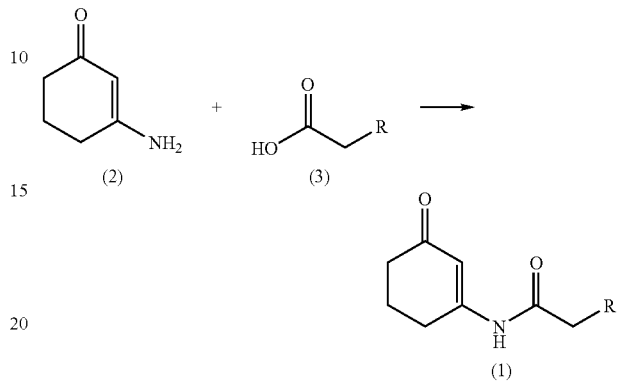

wherein R is the same as above, and X is a hydroxyl group or a halogen atom.

As shown in Reaction Formula 1 above, the amide compound of the Present Invention (1) can be prepared by reacting 3-amino-2-cyclohexene-1-one represented by Formula (2) (hereunder, this compound may be referred to as Compound (2)) with a carboxylic acid compound represented by General Formula (3) (hereunder, this compound may be referred to as Carboxylic Acid Compound (3)). The reaction between Compound (2) and Carboxylic Acid Compound (3) may be conducted in an inactive solvent in the presence of an appropriate condensing agent.

Examples of the condensing agents used in the above reaction include various known dehydrating condensing agents, including acid halide forming agents such as phosphorus trichloride, phosphorus tribromide, phosphorus pentachloride, phosphorus oxychloride, thionyl chloride; mixed acid anhydride forming agents such as ethyl chloroformate and chlorinated methane sulfonyl; carbodiimides such as N,N'-dicyclohexyl carbodiimide (DCC), diisopropyl carbodiimide, and 1-ethyl-3-dimethylaminopropyl carbodiimide; N,N-carbonyldiimidazole; 2-ethoxy-N-ethoxycarbonyl-1,2-dihydroquinoline (EEDQ); and triphenylphosphine-carbon tetrachloride (complex).

The amount of the condensing agent used in the reaction is generally about 0.8 to 5 mol, and preferably about 1 to 3 mol per mol of Carboxylic Acid Compound (3).

Various known solvents can be used as the inactive solvent in the above reaction in so far as they do not adversely affect the reaction. Examples of usable solvents include aromatic hydrocarbons such as benzene, toluene, and xylene; halogenated aromatic hydrocarbons such as chlorobenzene, and dichloro benzene; aliphatic and cycloaliphatic hydrocarbons such as n-hexane, cyclohexane, and petroleum ether; halogenated hydrocarbons such as dichloromethane, 1,2-chloroethane, chloroform, and carbon tetrachloride; ethers such as diethylether, diisopropylether, dioxane, tetrahydrofuran, ethyleneglycoldimethylether, and ethyleneglycoldiethylether; ketones such as acetone, 2-butanone, and methylisobutylketone; nitrites such as acetonitrile, propionitrile, and benzonitrile; amides such as N,N-dimethylformamide, and hexamethylphosphoric triamide (HMPA); sulfoxides such as dimethylsulfoxide; and mixtures of those solvents.

The amounts of Compound (2) and Carboxylic Acid Compound (3) used in the reaction can be selected from a wide range; for example, Compound (2) is generally used in the amount of 0.8 to 5 mol, and preferably 1 to 3 mol, per mol of the Carboxylic Acid Compound (3).

The reaction may be conducted while cooling, at room temperature, or while heating. Specifically, the reaction may be conduced in a range from −10° C. to a temperature not exceeding the boiling point of the solvent. The reaction time varies depending on the type and proportions of the reaction substrate, reaction time, and other conditions. However, the reaction is generally completed in about 5 to 10 hours.

The amide compound of the Present Invention (1) can also be produced, as shown in Reaction Formula 2 below, by reacting Compound (2) with a carboxylic acid halide represented by General Formula (4) (hereunder, this may be referred to as Carboxylic Acid Halide (4)) in an appropriate solvent, and if necessary, in the presence of a base.

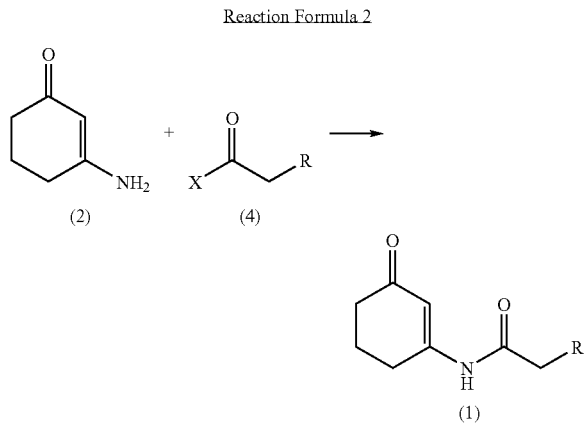

Reaction Formula 2 wherein R is the same as above, and X is a halogen atom.

The solvents usable in the reaction between Compound (2) and Carboxylic Acid Halide (4) are the same as those usable in the reaction between Compound (2) and Carboxylic Acid Compound (3) shown in the above Reaction Formula 1.

Various known bases are usable in the reaction. Specific examples thereof include alkali metal or alkaline-earth metal hydroxides such as sodium hydroxide, potassium hydroxide or calcium hydroxide; alkali metal carbonates or hydrogen carbonates such as sodium carbonate, potassium carbonate, sodium hydrogencarbonate, and potassium hydrogencarbonate; alkali metal or alkaline-earth metal acetates such as sodium acetate, potassium acetate, and calcium acetate; alkali metal or alkaline-earth metal hydrides such as sodium hydride, potassium hydride, and calcium hydride; ammonium salts such as ammonium hydroxide, ammonium bicarbonate, and ammonium acetate; and tertiary amines such as trimethyl amine, triethyl amine, N,N-dimethylaniline, pyridine, 4-(dimethylamino)pyridine, diaza-bicyclo-octane (DABCO), diaza-bicyclononene (DBN), and diaza-bicycloundecene (DBU).

The amount of base used in the reaction is generally about 1.0 to 2.0 mol, and preferably about 1.1 to 1.5 mol, per mol of Compound (2).

The proportion of Compound (2) to Carboxylic Acid Halide (4) may be selected from a wide range, and Compound (2) is generally used in the amount of about 0.8 to 5 mol, and preferably about 1 to 3 mol, per mol of Carboxylic Acid Halide (4).

The reaction may be conducted while cooling, at room temperature, or while heating. Specifically, the reaction may be conducted in a range from −10° C. to a temperature not exceeding the boiling point of the solvent. The reaction time varies depending on the type and proportions of the reaction substrate, reaction time, and other conditions. However, the reaction is generally completed in about 5 to 10 hours.

When R is a —CO($R^2$) group in Carboxylic Acid Halide (4) in Reaction Formula 1 and Carboxylic Acid Compound (3) in Reaction Formula 2, it is preferable that the carbonyl group be protected with an appropriate protective group before being supplied to the reaction.

There is no particular limitation to the protective groups used to protect the carbonyl group, and they can be suitably selected from the protective groups for a carbonyl group disclosed in Protective Groups in Organic Synthesis, Theodora W. Greene, 1981. After the amidation reaction shown in Reaction Formula 1 or Reaction Formula 2 is completed, a deprotection process suitable for the selected protective group is performed, thereby obtaining the target Amide Compound (1).

Note that Compound (2), Carboxylic Acid Compound (3) and Carboxylic Acid Halide (4) used in the above-described Reaction Formula 1 and Reaction Formula 2 are all commercially available or can be produced by a known method.

The Amide Compound (1) thus obtained can be easily refined by being isolated from the reaction mixture by conducting column chromatography, recrystallization or a like general isolation.

The amide compound of the present invention is effective for controlling infections caused by bacteria that belong to the *Erwinia* species, *Burkholderia* species or *Xanthomonas* species, such as *Xanthomonas oryzae* pv. *oryzae*, *Burkholderia glumae*, *Burkholderia plantarii*, *Burkholderia syringae*, *Xanthomonas campestris* pv. *citri*, *Erwinia amylovora*, *Xanthomonas campestris* pv. *pruni*, *Burkholderia syringae* pv. *morsprunorum*, *Xanthomonas campestris*, *Burkholderia syringae* pv. *maculicola*, *Erwinia carotovora*, *Burkholderia cicihorii*, *P. marginars*, *P. viridiflava*, *Erwinia carotovora* subsp. *cartovora*, and *Burkholderia solanacearum*, etc.). It is extremely effective for controlling *Burkholderia*, in particular, *Burkholderia glumae*.

When the amide compound of the present invention is used as a bactericide or a bacterial infection control agent for agricultural and horticultural use, the amide compound may be used as the control agent without any additives. However, the amide compound may also be used after being mixed with various carriers in a solid, liquid, gaseous or like form. If necessary, surfactants, binders, dispersants, stabilizers and like preparation adjuvants, etc., may be added to the amide compound so as to form emulsions, wettable powders, dry-flowable preparations, flowable preparations, water soluble preparations, granules, fine granules, parvules, powders, liniments, sprays, aerosols, microcapsules, fumigants, smoke fungicides, etc.

The content of the amide compound of the present invention, which is the active ingredient of these preparations, can be suitably selected from a broad range depending on various conditions, including their formulation, application site, etc. Generally, the content of the amide compound is about 0.01 to 95 wt. %, and preferably about 0.1 to 50 wt. % per total weight of the preparation.

Examples of solid carriers that may be mixed in the preparation of the present invention include kaolin clay, diatomaceous earth, bentonite, Fubasami clay, acid clay and like clays; talc, ceramics, cerite, quartz, sulfur, activated carbon, silica carbonate, silica hydrate and like inorganic minerals; chemical fertilizer and like fine powders; granular materials; etc.

Examples of liquid carriers that may be mixed in the preparation of the present invention include water; alcohol; acetone, methyl ethyl ketone and like ketones; n-hexane, cyclohexane, kerosene, light oil and like aliphatic or cycloaliphatic hydrocarbons; benzene, toluene, xylene, naphthalene and like aromatic hydrocarbons; ethyl acetate, butyl acetate and like esters; acetonitrile, isobutyronitrile and like nitriles; diisopropyl ether, dioxane and like ethers; N,N-dimethylformamide, N,N-dimethylacetamide and like acid amides; dichloromethane, trichloroethane, carbon tetrachloride and like halogenated hydrocarbons; dimethyl sulfoxide; soybean oil, cotton seed oil and like vegetable oils.

Examples of gaseous carriers that may be mixed in the preparation of the present invention include those generally used as propellants, such as butane gas, liquefied petroleum gas, dimethyl ether, and carbon dioxide gas.

Examples of surfactants that may be mixed in the preparation of the present invention include polyoxyethylene alkyl ether, polyoxyethylene alkyl ester, polyethylene sorbitan alkyl ester and like nonionic surfactants; alkylbenzene sulfonate, alkyl sulfosuccinate, alkyl sulfate, polyoxyethylene alkyl sulfate, allyl sulfonate, lignin sulfite and like anionic surfactants; etc.

Examples of binders and dispersants include casein, gelatin, polysaccharide (starch, gum arabic, cellulose derivatives, alginic acid, etc.), lignin derivatives, bentonite, saccharides, synthetic water-soluble polymers (polyvinyl alcohol, polyvinyl pyrrolidone, polyacrylic acids, etc.), etc.

Examples of stabilizers include PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oil, mineral oil, surfactant, fatty acid or an ester thereof, etc.

The preparation of the present invention may be colored using an organic dye and/or inorganic dye.

The preparation of the present invention may be used as it is or may be diluted with water or a like solvent. In the case of a granule, powder and the like, the preparation of the present invention is generally used without diluting. When an emulsion, wettable powder, flowable preparation and the like is diluted using water or a like solvent, the concentration of the active ingredient is generally about 0.0001 to 100 wt. %, and preferably about 0.001 to 10 wt. %.

The amide compound of the present invention may be pre-mixed with other agents such as a herbicide, insecticide, nematicide, miticide, bactericide, plant growth regulator, synergist, soil conditioner, etc. Furthermore, the preparation of the present invention may be used in combination with the above-mentioned agents.

Examples of methods for applying the amide compound of the present invention to cultivated plants include ground liquid spraying, ground solid spraying, aerial liquid spraying, aerial solid spraying, foliar spraying, use in a facility, soil incorporation, application during soil watering, surface treatment (seed coating, application treatment, etc.), seed box application, single flower treatment, root treatment, etc. Conventionally, seed treatment (disinfection) is often conducted to prevent bacterial plant infections. The amide compound of the present invention is also effective by conducting foliar application even after a bacterial infection is found. This allows various application methods to be employed.

The amount of the amide compound of the present invention is not particularly limited and can be selected from a wide range depending on various conditions, including the form of the preparation, the aspiration method, the application season, the application site, the type of farm products to which it is applied, the type of the targeted bacteria, and the like. The amount of the amide compound used is generally about 0.1 to 1,000 g and preferably about 10 to 500 g per 100 m$^2$. When an emulsion, wettable powder, flowable preparation or the like is diluted with water, the concentration is generally about 1 to 1,000 ppm, and preferably about 10 to 500 ppm. Granules, powders, etc., are usually used as they are without diluting.

Effect of the Invention

The amide compound of the present invention exhibits an excellent control effect against intractable bacterial plant infections. The amide compound of the present invention is remarkably effective for controlling the toxin production of, in particular, *Burkholderia glumae* and the like. Accordingly, the amide compound of the present invention is suitably usable as a bacterial infection control agent for agricultural and horticultural use.

BRIEF DESCRIPTION OF DRAWINGS

FIG. 1 is a graph showing the relationship between the concentrations (μM) of Compound (1a-3) and the comparative compound and toxin doses (μg/ml) in Test Example 1.

FIG. 2 is a graph showing the evaluation of the onset of *Burkholderia glumae* infection expressed as numerical values in terms of Compound (1a-3) in Test Example 2.

FIG. 3 is a graph showing the evaluation of onsets of *Burkholderia glumae* infection expressed as numerical values in terms of Compound (1a-3) in Test Example 3.

BEST MODE FOR CARRYING OUT THE INVENTION

The present invention is explained in detail below with reference to reference examples, production examples, formulation examples and a test example of the amide compound of the present invention. However, the scope of the present invention is not limited to these. Hereunder, Et stands for ethyl group; and the term "part" means "part by weight".

REFERENCE EXAMPLE 1

Production of 3,3-ethylene Glycosyl Hexanoyl Acid

(1) Production of ethyl 3-oxohexanoate

Meldrum's acid (2,2-dimethyl-1,3-dioxane-4,6-dione, 6.15 g, 42.7 mmol) and triethyl amine (8.63 g, 85.4 mmol) were dissolved in dichloromethane (60 mL). Butyric acid chloride (4.99 g, 46.9 mmol) was added to the solution thus obtained dropwise while cooling with ice, followed by stirring at room temperature for about 12 hours. The reaction mixture was concentrated under reduced pressure, and then the resulting residue was subjected to extraction using ethyl acetate. The thus-obtained organic layer was washed with dilute hydrochloric acid and an aqueous saturated sodium chloride solution, dried over magnesium sulfate, and then concentrated under reduced pressure. The resulting residue was purified using silica gel chromatography (developing solvent: n-hexane/ethyl acetate=8/2) to obtain 5-butyl-2,2-dimethyl-1,3-dioxane-4,6-dione.

The 5-butyl-2,2-dimethyl-1,3-dioxane-4,6-dione thus obtained was allowed to reflux in ethanol for 2 hours, and then concentrated under reduced pressure. The resulting residue was purified using silica gel chromatography (developing solvent: n-hexane/ethyl acetate=8/2) to obtain the ethyl 3-oxohexanoate shown by the formula below.

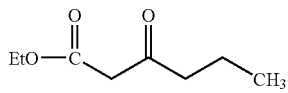

Quantity Yield: 4.85 g (30.7 mmol)

Percent Yield: 72%

$^1$H-NMR (CDCl$_3$, 500 MHz); 0.94 ppm (t, 3H), 1.30 ppm (t, 3H), 1.66 ppm (m, 2H), 2.54 ppm (m, 2H), 3.45 ppm (s, 2H), 4.22 ppm (q, 2H).

(2) Production of ethyl 3,3-ethylene Glycosyl Hexanoate

Ethyl 3-oxohexanoate (4.00 g, 25.3 mmol) obtained in (1) above, ethylene glycol (7.84 g, 126.5 mmol) and p-toluenesulfonic acid monohydrate (475 mg, 2.5 mmol) were dissolved in benzene (50 mL), and allowed to reflux using a reflux apparatus equipped with a Dean Stark device for 6 hours. After cooling, the thus-obtained organic layer was washed with an aqueous saturated sodium bicarbonate solution, dried over magnesium sulfate, and then concentrated under reduced pressure. The resulting residue was purified using silica gel chromatography (developing solvent: n-hexane/ethyl acetate=6/4) to obtain the ethyl 3,3-ethylene glycosyl hexanoate shown by the formula below.

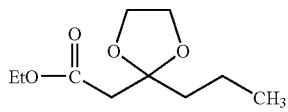

Quantity Yield: 4.48 g (22.2 mmol)

Percent Yield: 88%

$^1$H-NMR (CDCl$_3$, 500 MHz); 0.94 ppm (t, 3H), 1.29 ppm (t, 3H), 1.45 ppm (m, 2H), 1.81 ppm (m, 2H), 2.67 ppm (s, 2H), 4.00 ppm (m, 4H), 4.20 ppm (q, 2H).

(3) Production of 3,3-ethylene Glycosyl Hexanoyl Acid

Ethyl 3,3-ethylene glycosyl hexanoate (4.48 g, 22.2 mmol) obtained in (2) above and lithium hydroxide monohydrate (4.66 g, 111 mmol) were dissolved in a mixed solution of tetrahydrofuran (50 mL) and distilled water (50 mL), followed by stirring at room temperature for about 12 hours. The reaction mixture thus obtained was neutralized with diluted hydrochloric acid, and then concentrated under reduced pressure. The resulting residue was subjected to extraction using ethyl acetate. The thus-obtained organic layer was washed with an aqueous saturated sodium chloride solution, dried over magnesium sulfate, and then concentrated under reduced pressure. The resulting residue was purified using silica gel chromatography (developing solvent: ethyl acetate/methanol=2/8) to obtain the 3,3-ethylene glycosyl hexanoyl acid shown by the formula below.

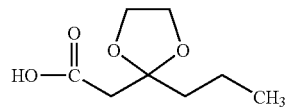

Quantity Yield: 2.31 g (13.3 mmol)

Percent Yield: 60%

$^1$H-NMR (CDCl$_3$, 500 MHz); 0.69 ppm (t, 3H), 1.17 ppm (m, 2H), 1.55 ppm (m, 2H), 2.32 ppm (s, 2H), 3.80 ppm (m, 4H).

REFERENCE EXAMPLE 2

Production of 3,3-ethylene Glycosyl Octanoyl Acid

(1) Production of ethyl 3-oxo-octanoate

Meldrum's acid (6.15 g, 42.7 mmol) and triethyl amine (8.63 g, 85.4 mmol) were dissolved in dichloromethane (75 mL). Hexanoic acid chloride (6.31 g, 46.9 mmol) was added to the resulting mixture dropwise while cooling with ice, followed by stirring at room temperature for about 12 hours. The reaction mixture thus obtained was concentrated under reduced pressure, and the resulting residue was then subjected to extraction using ethyl acetate. The thus-obtained organic layer was washed with diluted hydrochloric acid and an aqueous saturated sodium chloride solution, dried over magnesium sulfate, and then concentrated under reduced pressure. The resulting residue was purified using silica gel chromatography (developing solvent: n-hexane/ethyl acetate=8/2) to obtain 5-hexanoly-2,2-dimethyl-1,3-dioxane-4,6-dione.

The resulting 5-hexanoly-2,2-dimethyl-1,3-dioxane-4,6-dione was allowed to reflux in ethanol for 2 hours, and then concentrated under reduced pressure. The resulting residue was purified using silica gel chromatography (developing solvent: n-hexane/ethyl acetate=8/2) to obtain ethyl 3-oxo-octanoate.

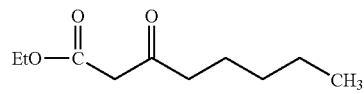

Quantity Yield: 7.45 g (40.1 mmol)

Percent Yield: 94%

$^1$H-NMR (CDCl$_3$, 500 MHz); 0.91 ppm (t, 3H), 1.25 ppm (m, 7H), 1.62 ppm (m, 2H), 2.54 ppm (m, 2H), 3.45 ppm (s, 2H), 4.20 ppm (q, 2H).

(2) Production of ethyl 3,3-ethylene Glycosyl Octanoate

Ethyl 3-oxo-octanoate (6.01 g, 32.3 mmol) obtained in (1) above, ethylene glycol (10.01 g, 161.5 mmol) and p-toluenesulfonic acid monohydrate (627 mg, 3.3 mmol) were dissolved in benzene (50 mL), and allowed to reflux using a reflux apparatus equipped with a Dean Stark device for 6 hours. After cooling, the thus-obtained organic layer was washed with an aqueous saturated sodium bicarbonate solution, dried over magnesium sulfate, and then concentrated under reduced pressure. The resulting residue was purified using silica gel chromatography (developing solvent: n-hexane/ethyl acetate=6/4) to obtain the ethyl 3,3-ethylene glycosyl octanoate shown by the formula below.

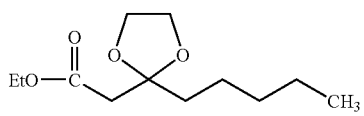 [SMILES: CCCCCC1(CC(=O)OCC)OCCO1]

Quantity Yield: 6.83 g (29.7 mmol)
Percent Yield: 92%
$^1$H-NMR (CDCl$_3$, 500 MHz); 0.91 ppm (t, 3H), 1.29 ppm (m, 7H), 1.33 ppm (m, 2H), 1.74 ppm (m, 2H), 2.67 ppm (s, 2H), 4.01 ppm (m, 4H), 4.19 ppm (q, 2H).

(3) Production of 3,3-ethylene Glycosyl Octanoyl Acid

Ethyl 3,3-ethylene glycosyl octanoate (6.83 g, 29.7 mmol) obtained in (2) above and lithium hydroxide monohydrate (6.24 g, 148.5 mmol) were dissolved in a mixed solution of tetrahydrofuran (50 mL) and distilled water (50 mL), followed by stirring at room temperature for about 12 hours. The reaction mixture was neutralized with diluted hydrochloric acid, and then concentrated under reduced pressure. The resulting residue was subjected to extraction with ethyl acetate. The organic layer thus obtained was washed with an aqueous saturated sodium chloride solution, dried over magnesium sulfate, and then concentrated under reduced pressure. The resulting residue was purified using silica gel chromatography (developing solvent: ethyl acetate/methanol=2/8) to obtain the 3,3-ethylene glycosyl octanoyl acid shown by the formula below.

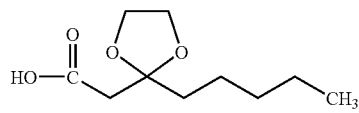

Quantity Yield: 4.75 g (23.5 mmol)
Percent Yield: 79%
$^1$H-NMR (CDCl$_3$, 500 MHz); 0.84 ppm (t, 3H), 1.22 ppm (m, 4H), 1.30 ppm (m, 2H), 1.66 ppm (m, 2H), 2.65 ppm (s, 2H), 3.97 ppm (m, 4H).

REFERENCE EXAMPLE 3

Production of 3,3-ethylene Glycosyl Decanoyl Acid (1) Production of ethyl 3-oxodecanoate Meldrum's acid (6.15 g, 42.7 mmol) and triethyl amine (8.63 g, 85.4 mmol) were dissolved in dichloromethane (75 mL).
Octanoic acid chloride (7.62 g, 46.9 mmol) was added to the resulting mixture dropwise while cooling with ice, followed by stirring at room temperature for about 12 hours. The reaction mixture thus obtained was then concentrated under reduced pressure. The resulting organic layer was washed with diluted hydrochloric acid and an aqueous saturated sodium chloride solution, dried over magnesium sulfate, and then concentrated under reduced pressure. The resulting residue was purified using silica gel chromatography (developing solvent: n-hexane/ethyl acetate=8/2) to obtain 5-octanoyl-2,2-dimethyl-1,3-dioxane-4,6-dione.

The resulting 5-octanoyl-2,2-dimethyl-1,3-dioxane-4,6-dione was allowed to reflux in ethanol for 2 hours, and then concentrated under reduced pressure. The resulting residue was purified using silica gel chromatography (developing solvent: n-hexane/ethyl acetate=8/2) to obtain ethyl 3-oxodecanoate shown by the formula below.

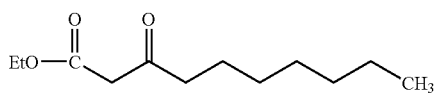

Quantity Yield: 8.22 g (38.4 mmol)
Percent Yield: 90%
$^1$H-NMR (CDCl$_3$, 500 MHz); 0.91 ppm (t, 3H), 1.30 ppm (m, 11H), 1.62 ppm (m, 2H), 2.55 ppm (m, 2H), 3.46 ppm (s, 2H), 4.20 ppm (q, 2H).

(2) Production of ethyl 3,3-ethylene Glycosyl Decanoate

Ethyl 3-oxodecanoate (5.99 g, 28 mmol) obtained in (1) above, ethylene glycol (8.68 g, 140 mmol) and p-toluenesulfonic acid monohydrate (532 mg, 2.8 mmol) were dissolved in benzene (50 mL), and allowed to reflux using a reflux apparatus equipped with a Dean Stark device for 6 hours. After cooling, the thus-obtained organic layer was washed with an aqueous saturated sodium bicarbonate solution, dried over magnesium sulfate, and then concentrated under reduced pressure. The resulting residue was purified using silica gel chromatography (developing solvent: n-hexane/ethyl acetate=6/4) to obtain the ethyl 3,3-ethylene glycosyl decanoate shown by the formula below.

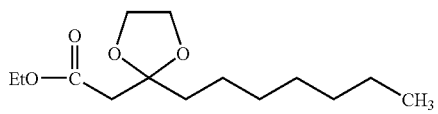 [SMILES: CCCCCCCC1(CC(=O)OCC)OCCO1]

Quantity Yield: 6.50 g (25.2 mmol)
Percent Yield: 90%
$^1$H-NMR (CDCl$_3$, 500 MHz); 0.91 ppm (t, 3H), 1.29 ppm (m, 11H), 1.33 ppm (m, 2H), 1.81 ppm (m, 2H), 2.67 ppm (s, 2H), 4.01 ppm (m, 4H), 4.19 ppm (q, 2H).

(3) Production of 3,3-ethylene Glycosyl Decanoyl Acid

Ethyl 3,3-ethylene glycosyl decanoate (6.50 g, 25.2 mmol) obtained in (2) above and lithium hydroxide monohydrate (5.29 g, 126 mmol) were dissolved in a mixed solution of tetrahydrofuran (50 mL) and distilled water (50 mL), followed by stirring at room temperature for about 12 hours. The reaction mixture was neutralized with diluted hydrochloric acid, and then concentrated under reduced pressure. The resulting residue was subjected to extraction with ethyl acetate. The organic layer thus obtained was washed with an aqueous saturated sodium chloride solution, dried over magnesium sulfate, and then concentrated under reduced pressure. The resulting residue was purified using silica gel chromatography (developing solvent: ethyl acetate/methanol=2/8) to obtain the 3,3-ethylene glycosyl decanoyl acid shown by the formula below.

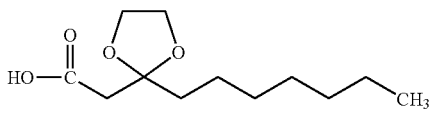

Quantity Yield: 4.05 g (17.6 mmol)
Percent Yield: 70%
$^1$H-NMR (CDCl$_3$, 500 MHz); 0.84 ppm (t, 3H), 1.22 ppm (m, 8H), 1.33 ppm (m, 2H), 1.76 ppm (m, 2H), 2.65 ppm (s, 2H), 3.97 ppm (m, 4H).

REFERENCE EXAMPLE 4

Production of 3,3-ethylene Glycosyl Dodecanoyl Acid (1) Production of ethyl 3-oxododecanoate Meldrum's acid (7.20 g, 50 mmol) and triethyl amine (5.56 g, 55 mmol) were dissolved in dichloromethane (50 mL), and decanoic acid chloride (10.48 g, 55 mmol) was added to the resulting mixture dropwise while cooling with ice. The reaction mixture was stirred at room temperature for about 12 hours, and then concentrated under reduced pressure. The ethyl acetate layer thus obtained was washed with diluted hydrochloric acid and an aqueous saturated sodium chloride solution, dried over magnesium sulfate, and then concentrated under reduced pressure. The resulting residue was purified using silica gel chromatography (developing solvent: n-hexane/ethyl acetate=3/7) to obtain 5-decanoyl-2,2-dimethyl-1,3-dioxane-4,6-dione.

The resulting 5-decanoyl-2,2-dimethyl-1,3-dioxane-4,6-dione was allowed to reflux in ethanol for 2 hours, and then concentrated under reduced pressure. The resulting residue was purified using silica gel chromatography (developing solvent: n-hexane/ethyl acetate=3/7) to obtain the ethyl 3-oxododecanoate shown by the formula below.

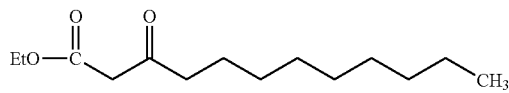 [SMILES: CCCCCCCCCC(=O)CC(=O)OCC]

Quantity Yield: 11.85 g (48.9 mmol)
Percent Yield: 98%
$^1$H-NMR (CDCl$_3$, 500 MHz); 0.91 ppm (t, 3H), 1.30 ppm (m, 15H), 1.62 ppm (m, 2H), 2.55 ppm (m, 2H), 3.45 ppm (s, 2H), 4.20 ppm (q, 2H).

(2) Production of 3,3-ethylene Glycosyl Dodecanoyl Acid

Ethyl 3-oxododecanoate (6.05 g, 25 mmol) obtained in (1) above, ethylene glycol (7.75 g, 125 mmol), and p-toluenesulfonic acid monohydrate (0.48 g, 2.5 mmol) were dissolved in benzene (50 mL), and allowed to reflux using a reflux apparatus equipped with a Dean Stark device for 6 hours. After cooling, the thus-obtained organic layer was washed with an aqueous saturated sodium bicarbonate solution, dried over magnesium sulfate, and then concentrated under reduced pressure. The resulting residue was purified using silica gel chromatography (developing solvent: n-hexane/ethyl acetate=5/5) to obtain the ethyl 3,3-ethylene glycosyl dodecanoate shown by the formula below.

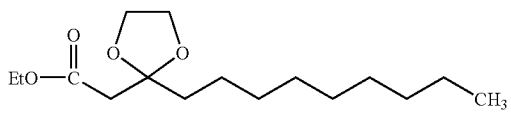 [SMILES: CCCCCCCCCC1(CC(=O)O)OCCO1]

Quantity Yield: 6.99 g (24.5 mmol)
Percent Yield: 98%
$^1$H-NMR (CDCl$_3$, 500 MHz); 0.91 ppm (t, 3H), 1.29 ppm (m, 15H), 1.33 ppm (m, 2H), 1.81 ppm (m, 2H), 2.67 ppm (s, 2H), 4.01 ppm (m, 4H), 4.19 ppm (q, 2H).

(3) Production of 3,3-ethylene Glycosyl Dodecanoyl Acid

Ethyl 3,3-ethylene glycosyl dodecanoate (5.72 g, 20 mmol) obtained in (2) above and lithium hydroxide monohydrate (4.20 g, 100 mmol) were dissolved in a mixed solution of tetrahydrofuran (50 mL) and distilled water (50 mL), followed by stirring at room temperature for about 12 hours. The resulting reaction mixture was neutralized with diluted hydrochloric acid, and then concentrated under reduced pressure. The organic layer thus obtained was washed with an aqueous saturated sodium chloride solution, dried over magnesium sulfate, and then concentrated under reduced pressure. The resulting residue was purified using silica gel chromatography (developing solvent: ethyl acetate/methanol=3/7) to obtain 3,3-ethylene glycosyl dodecanoyl acid.

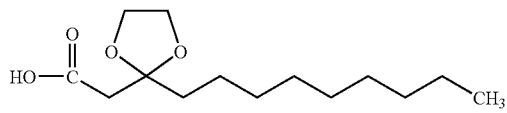

Quantity Yield: 3.71 g (14.4 mmol)
Percent Yield: 72%
$^1$H-NMR (CDCl$_3$, 500 MHz); 0.84 ppm (t, 3H), 1.22 ppm (m, 12H), 1.33 ppm (m, 2H), 1.76 ppm (m, 2H), 2.65 ppm (s, 2H), 3.97 ppm (m, 4H).

PRODUCTION EXAMPLE 1

Production of N-(3-oxo-cyclohexen-1-yl) butyramide (1a-1)

Butyric acid (465 mg, 5.28 mmol) and 3-amino-2-cyclohexene-1-one (645 mg, 5.81 mmol) were dissolved in dichloromethane (50 mL). Dimethylaminopyridine (750 mg, 5.81 mmol), diisopropylethylamine (774 mg, 6.34 mmol) and 1-ethyl-3-dimethylaminopropyl carbodiimide (1.13 g, 5.81 mmol) were added to the resulting mixture, followed by stirring at room temperature for about 14 hours. The reaction mixture was concentrated under reduced pressure. The resulting residue was purified using silica gel chromatography (developing solvent: n-hexane/ethyl acetate=6/4) to obtain the N-(3-oxo-cyclohexen-1-yl)butyramide (1a-1) shown by the formula below.

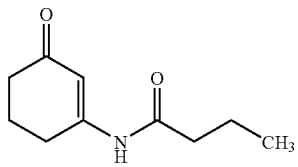

(1a-1)

Quantity Yield: 97 mg (0.54 mmol)

Percent Yield: 10%

$^1$H-NMR (CDCl$_3$, 500 MHz): 0.98 ppm (t, 3H), 1.71 ppm (m, 2H), 2.06 ppm (m, 2H), 2.36 ppm (m, 4H), 2.61 ppm (m, 2H), 6.59 ppm (s, 1H), 7.47 ppm (br, 1H).

PRODUCTION EXAMPLE 2

Production of N-(3-oxo-cyclohexen-1-yl)hexanamide (1a-2)

N-(3-oxo-cyclohexen-1-yl)hexanamide (1a-2) was produced in the same manner as in Production Example 1 except that n-hexanoic acid was used instead of butyric acid.

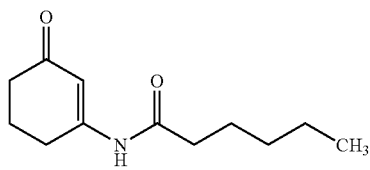

(1a-2)

Quantity Yield: 319 mg (1.53 mmol)

Percent Yield: 38%

$^1$H-NMR (CDCl$_3$, 500 MHz): 0.93 ppm (t, 3H), 1.34 ppm (m, 4H), 1.70 ppm (m, 2H), 2.06 ppm (m, 2H), 2.37 ppm (m, 4H), 2.60 ppm (m, 2H), 6.55 ppm (s, 1H), 7.06 ppm (br, 1H).

PRODUCTION EXAMPLE 3

Production of AT-(3-oxo-cyclohexen-1-yl)octanamide (1a-3)

N-(3-oxo-cyclohexen-1-yl)octanamide (1a-3) was produced in the same manner as in Production Example 1 except that octanoic acid was used instead of butyric acid.

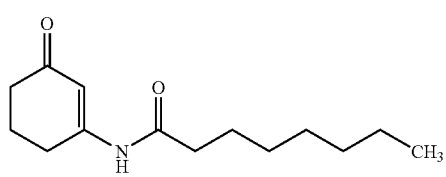

(1a-3)

Quantity Yield: 15.53 g (65.5 mmol)

Percent Yield: 39%

$^1$H-NMR (CDCl$_3$, 500 MHz): 0.90 ppm (t, 3H), 1.31 ppm (m, 8H), 1.68 ppm (m, 2H), 2.06 ppm (m, 2H), 2.38 ppm (m, 4H), 2.62 ppm (m, 2H), 6.57 ppm (s, 1H), 7.33 ppm (br, 1H).

PRODUCTION EXAMPLE 4

Production of N-(3-oxo-cyclohexen-1-yl)decanamide (1a-4)

N-(3-oxo-cyclohexen-1-yl)decanamide (1a-4) was produced in the same manner as in Production Example 1 except that decanoic acid was used instead of butyric acid.

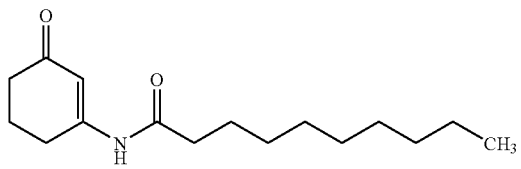

(1a-4)

Quantity Yield: 575 mg (2.17 mmol)

Percent Yield: 41%

$^1$H-NMR (CDCl$_3$, 500 MHz): 0.90 ppm (t, 3H), 1.28 ppm (m, 12H), 1.68 ppm (m, 2H), 2.06 ppm (m, 2H), 2.38 ppm (m, 4H), 2.61 ppm (m, 2H), 6.57 ppm (s, 1H), 7.38 ppm (br, 1H).

PRODUCTION EXAMPLE 5

Production of N-(3-oxo-cyclohexen-1-yl)dodecanamide (1a-5)

N-(3-oxo-cyclohexen-1-yl)dodecanamide (1a-5) was produced in the same manner as in Production Example 1 except that dodecanoic acid was used instead of butyric acid.

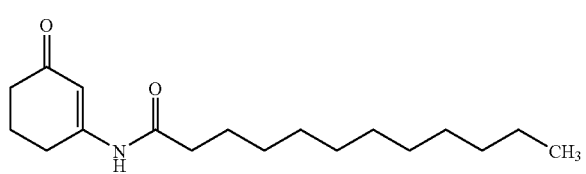

(1a-5)

Quantity Yield: 281 mg (0.96 mmol)

Percent Yield: 32%

$^1$H-NMR (CDCl$_3$, 500 MHz): 0.90 ppm (t, 3H), 1.28 ppm (m, 16H), 1.68 ppm (m, 2H), 2.06 ppm (m, 2H), 2.39 ppm (m, 4H), 2.61 ppm (m, 2H), 6.61 ppm (s, 1H), 7.27 ppm (br, 1H).

PRODUCTION EXAMPLE 6

Production of 3-oxo-N-(3-oxo-cyclohexen-1-yl)hexanamide (1b-1)

(1) Production of N-(3-oxo-cyclohexen-1-yl)-3,3-ethylene Glycosyl Hexanamide

N-(3-oxo-cyclohexen-1-yl)-3,3-ethylene glycosyl hexanamide shown by the formula below was produced in the same manner as in Production Example 1 except that 3,3-ethylene glycosyl hexanoyl acid obtained in Reference Example 1 was used instead of butyric acid.

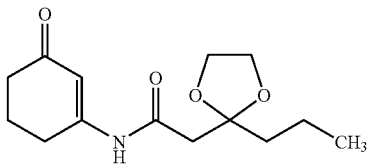 [SMILES: CCCC1(CC(=O)NC2=CC(=O)CCC2)OCCO1]

Quantity Yield: 283 mg (1.06 mmol)

Percent Yield: 24%

$^{1}$H-NMR (CDCl$_3$, 500 MHz): 0.91 ppm (t, 3H), 1.70 ppm (m, 2H), 2.08 ppm (m, 2H), 2.41 ppm (m, 2H), 2.59 ppm (m, 4H), 2.76 ppm (s, 2H), 4.15 ppm (m, 4H), 6.74 ppm (s, 1H), 9.03 ppm (br, 1H).

(2) Production of 3-oxo-N-(3-oxo-cyclohexen-1-yl)hexanamide (1b-1)

Trifluoroacetic acid (2 mL) was added to the above-obtained N-(3-oxo-cyclohexen-1-yl)-3,3-ethylene glycosyl hexanamide (283 mg, 1.06 mmol), followed by stirring at room temperature for about 18 hours. The resulting reaction mixture was neutralized with a 5% aqueous sodium hydroxide solution, and then subjected to extraction using ethyl acetate. The organic layer thus obtained was well-washed with saturated sodium bicarbonate solution, dried over magnesium sulfate, and then concentrated under reduced pressure. The resulting residue was purified using silica gel chromatography (developing solvent: n-hexane/ethyl acetate=3/7), obtaining 3-oxo-N-(3-oxo-cyclohexen-1-yl)hexanamide (1b-1).

(1b-1)

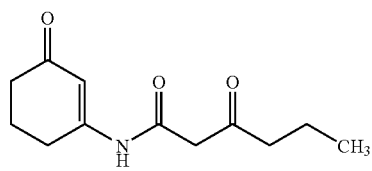

Quantity Yield: 127.8 mg (0.57 mmol)

Percent Yield: 54%

$^{1}$H-NMR (CDCl$_3$, 500 MHz); 0.91 ppm (t, 3H), 1.70 ppm (m, 2H), 2.08 ppm (m, 2H), 2.41 ppm (m, 2H), 2.59 ppm (m, 4H), 3.55 ppm (s, 2H), 6.74 ppm (s, 1H), 9.11 ppm (br, 1H).

PRODUCTION EXAMPLE 7

Production of 3-oxo-N-(3-oxo-cyclohexen-1-yl)octanamide (1b-2)

(1) Production of N-(3-oxo-cyclohexen-1-yl)-3,3-ethylene Glycosyl Octanamide

N-(3-oxo-cyclohexen-1-yl)-3,3-ethylene glycosyl octanamide shown by the formula below was produced in the same manner as in Production Example 1 except that 3,3-ethylene glycosyl octanoyl acid obtained in Reference Example 1 was used instead of butyric acid.

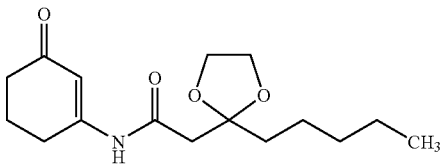 [SMILES: CCCCCC1(CC(=O)NC2=CC(=O)CCC2)OCCO1]

Quantity Yield: 310 mg (1.05 mmol)

Percent Yield: 26%

$^{1}$H-NMR (CDCl$_3$, 500 MHz): 0.93 ppm (t, 3H), 1.32 ppm (m, 4H), 1.64 ppm (m, 2H), 2.08 ppm (m, 2H), 2.34 ppm (m, 2H), 2.59 ppm (m, 4H), 2.75 ppm (s, 2H), 4.13 ppm (m, 4H), 6.74 ppm (s, 1H), 9.08 ppm (br, 1H).

(2) Production of 3-oxo-N-(3-oxo-cyclohexen-1-yl)octanamide (1b-2)

Trifluoroacetic acid (2 mL) was added to the above-obtained N-(3-oxo-cyclohexen-1-yl)-3,3-ethylene glycosyl octanamide (310 mg, 1.05 mmol), followed by stirring at room temperature for about 18 hours. The resulting reaction mixture was neutralized by a 5% aqueous sodium hydroxide solution, and then subjected to extraction using ethyl acetate. The organic layer thus obtained was well-washed with a saturated sodium bicarbonate solution, dried over magnesium sulfate, and then concentrated under reduced pressure. The resulting residue was purified using silica gel chromatography (developing solvent: n-hexane/ethyl acetate=3/7), obtaining 3-oxo-N-(3-oxo-cyclohexen-1-yl)octanamide (1b-2).

(1b-2)

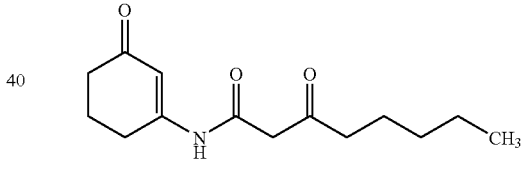

Quantity Yield: 98 mg (0.39 mmol)

Percent Yield: 37%

$^{1}$H-NMR (CDCl$_3$, 500 MHz): 0.93 ppm (t, 3H), 1.32 ppm (m, 4H), 1.64 ppm (m, 2H), 2.08 ppm (m, 2H), 2.34 ppm (m, 2H), 2.59 ppm (m, 4H), 3.55 ppm (s, 2H), 6.74 ppm (s, 1H), 9.12 ppm (br, 1H).

PRODUCTION EXAMPLE 8

Production of 3-oxo-N-(3-oxo-cyclohexen-1-yl)decanamide (1b-3)

(1) Production of N-(3-oxo-cyclohexen-1-yl)-3,3-ethylene Glycosyl Decanamide

N-(3-oxo-cyclohexen-1-yl)-3,3-ethylene glycosyl decanamide shown by the formula below was produced in the same manner as in Production Example 1 except that 3,3-ethylene glycosyl decanoyl acid obtained in Reference Example 1 was used instead of butyric acid.

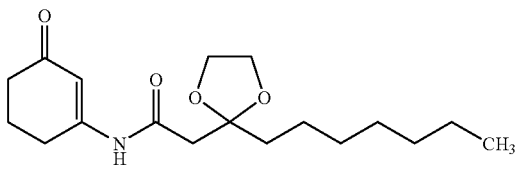 [SMILES: CCCCCCCC1(CC(=O)NC2=CC(=O)CCC2)OCCO1]

Quantity Yield: 384 mg (1.19 mmol)

Percent Yield: 30%

$^1$H-NMR (CDCl$_3$, 500 MHz): 0.88 ppm (t, 3H), 1.27 ppm (m, 8H), 1.61 ppm (m, 2H), 2.05 ppm (m, 2H), 2.38 ppm (m, 2H), 2.55 ppm (m, 4H), 2.71 ppm (s, 2H), 4.06 ppm (m, 4H), 6.71 ppm (s, 1H), 9.01 ppm (br, 1H).

(2) Production of 3-oxo-N-(3-oxo-cyclohexen-1-yl) decanamide (1b-3)

Trifluoroacetic acid (2 mL) was added to the above-obtained N-(3-oxo-cyclohexen-1-yl)-3,3-ethylene glycosyl decanamide (384 mg, 1.19 mmol), followed by stirring at room temperature for about 18 hours. The resulting reaction mixture was neutralized by a 5% aqueous sodium hydroxide solution, and subjected to extraction using ethyl acetate. The organic layer thus obtained was well-washed with a saturated sodium bicarbonate solution, dried over magnesium sulfate, and then concentrated under reduced pressure. The resulting residue was purified using silica gel chromatography (developing solvent: n-hexane/ethyl acetate=3/7), obtaining 3-oxo-N-(3-oxo-cyclohexen-1-yl)decanamide (1b -3).

(1b-3)

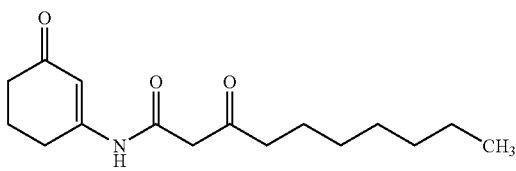

Quantity Yield: 190 mg (0.68 mmol)

Percent Yield: 57%

$^1$H-NMR (CDCl$_3$, 500 MHz); 0.88 ppm (t, 3H), 1.27 ppm (m, 8H), 1.61 ppm (m, 2H), 2.05 ppm (m, 2H), 2.38 ppm (m, 2H), 2.55 ppm (m, 4H), 3.52 ppm (s, 2H), 6.71 ppm (s, 1H), 9.10 ppm (br, 1H).

PRODUCTION EXAMPLE 9

Production of 3-oxo-N-(3-oxo-cyclohexen-1-yl) dodecanamide (1b-4)

(1) Production of N-(3-oxo-cyclohexen-1-yl)-3,3-ethylene Glycosyl Dodecanamide

N-(3-Oxo-cyclohexen-1-yl)-3,3-ethylene glycosyl dodecanamide shown by the formula below was produced in the same manner as in Production Example 1 except that 3,3-ethylene glycosyl decanoyl acid obtained in Reference Example 1 was used instead of butyric acid.

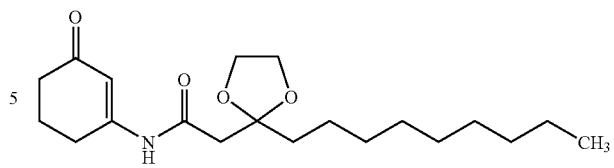

Quantity Yield: 249 mg (0.71 mmol)
Percent Yield: 36%
$^1$H-NMR (CDCl$_3$, 500 MHz): 0.89 ppm (t, 3H), 1.27 ppm (m, 12H), 1.61 ppm (m, 2H), 2.06 ppm (m, 2H), 2.38 ppm (m, 2H), 2.55 ppm (m, 4H), 2.71 ppm (s, 2H), 4.08 ppm (m, 4H), 6.72 ppm (s, 1H), 9.00 ppm (br, 1H).

(2) Production of 3-oxo-N-(3-oxo-cyclohexen-1-yl) dodecanamide (1b-4)

Trifluoroacetic acid (2 mL) was added to the above-obtained N-(3-oxo-cyclohexen-1-yl)-3,3-ethylene glycosyl dodecanamide (249 mg, 0.71 mmol), followed by stirring at room temperature for about 18 hours. The resulting reaction mixture was neutralized by a 5% aqueous sodium hydroxide solution, and subjected to extraction using ethyl acetate. The organic layer thus obtained was well-washed with a saturated sodium bicarbonate solution, dried over magnesium sulfate, and then concentrated under reduced pressure. The resulting residue was purified using silica gel chromatography (developing solvent: n-hexane/ethyl acetate=3/7), obtaining 3-oxo-N-(3-oxo-cyclohexen-1-yl)dodecanamide (1b-4).

(1b-4)

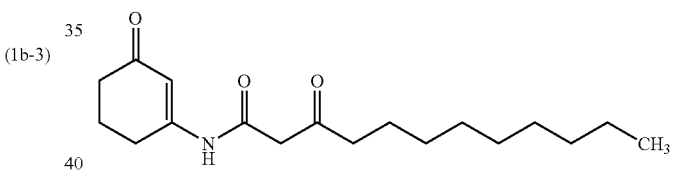

Quantity Yield: 33.8 mg (0.12 mmol)
Percent Yield: 17%
$^1$H-NMR (CDCl$_3$, 500 MHz); 0.89 ppm (t, 3H), 1.27 ppm (m, 12H), 1.61 ppm (m, 2H), 2.06 ppm (m, 2H), 2.38 ppm (m, 2H), 2.55 ppm (m, 4H), 3.52 ppm (s, 2H), 6.72 ppm (s, 1H), 9.10 ppm (br, 1H).

FORMULATION EXAMPLE 1

Emulsion

Each of the amide compounds (10 parts of each) of the present invention obtained in Production Examples 1-9 was dissolved in 45 parts of Solvesso 150 and 35 parts of N-methyl pyrrolidone. An emulsifier (product name: Solpol 3005X, Toho Chemical Industry Co., Ltd., 10 parts) was added to each of the resulting mixtures, followed by stirring. A 10% emulsion of each of the amide compounds of the present invention was thus obtained.

FORMULATION EXAMPLE 2

Wettable Powder

Each of the amide compounds (20 parts of each) of the present invention obtained in Production Examples 1-9 was added to a mixture of laurylsodium sulfate (2 parts), sodium ligninsulfonate (4 parts), synthesized hydrous silicon oxide fine powder (20 parts) and clay (54 parts). The resulting mixture was stirred and mixed using a juice mixer, obtaining a 20% wettable powder.

FORMULATION EXAMPLE 3

Granule

Sodium dodecylbenzene sulphonate (2 parts), bentonite (10 parts) and clay (83 parts) were added to each of the amide compounds (5 parts of each) of the present invention obtained in Production Examples 1-9, followed by sufficient stirring and mixing. An adequate amount of water was added to the resulting mixture. The reaction mixture was further stirred, granulated using a granulator, and then subjected to air drying, obtaining 5% granules.

FORMULATION EXAMPLE 4

Powder

Each of the amide compounds (1 part of each) of the present invention obtained in Production Examples 1-9 was dissolved in an adequate amount of acetone. Synthesized hydrous silicon oxide fine powder (5 parts), PAP (acidic isopropyl phosphate, 0.3 part) and clay (93.7 parts) were added thereto. The resulting mixture was stirred and mixed using a juice mixer, and acetone was removed therefrom by evaporation, obtaining 1% powder.

FORMULATION EXAMPLE 5

Flowable Preparation

Each of the amide compounds (20 parts of each) of the present invention obtained in Production Examples 1-9 was mixed with water (20 parts) containing polyoxyethylene tristyryl phenyl ether phosphoric ester triethanol amine (3 parts) and a silicone-based antifoaming agent (product name: Rhodorsil 426R, manufactured by RHODIA CHIMIE, 0.2 part). The mixture was subjected to wet grinding using a mill (product name: Dyno-Mill, manufactured by Willy A. Bachofen), and then mixed with water (60 parts) containing propylene glycol (8 parts) and xanthan gum (0.32 part), obtaining a 20% water suspension.

TEST EXAMPLE 1

*Burkholderia glumae* was inoculated into an LB culture medium (produced by BD, Difco LB Broth: containing tryptone (10.0 g), yeast extract (5.0 g), and sodium chloride (10.0 g)), and cultured at 37° C. overnight. The broth thus obtained was subjected to bacterial collection using a centrifuge, and the collected bacteria were washed with an LB culture medium twice using a fresh LB culture medium each time. A fresh LB culture medium was added to the bacteria, and then Compound (1a-3) produced in Production Example 3 was added thereto in such a manner that its final concentration became a predetermined value (i.e., 0, 20, 40, 60, 80 or 100 μM), followed by shake culturing for 20 hours. The amount of toxoflavin produced by the bacteria in the broth was obtained by the following procedure.

Each broth was filtered by a 0.22-μm membrane filter, and 1 mL of the filtrate was isolated. One mL of chloroform was added to the filtrate, followed by extraction. The thus-obtained chloroform layer was concentrated under reduced pressure, and an 80% (V/V) aqueous methanol solution was added to and dissolved in the residue. The absorbance (at 260 nm) of the solution was measured, and the toxin doses were calculated from the calibration curve, which was obtained using a chemically synthesized standard toxin.

The same test was conducted as a comparative test using the compound (comparative compound) shown by the formula below disclosed in Patent Document 1. FIG. 1 shows the results.

(Comparative Compound)

As is clear from FIG. 1, when Amide Compound (1a-3) of the present invention produced in Production Example 3 was added to *Burkholderia glumae*, the toxin doses produced by bacteria remarkably decreased as the concentration of Amide Compound (1a-3) increased. In contrast, when a comparative compound was added to *Burkholderia glumae*, the toxin doses produced by bacteria exhibited almost no change even when the concentration of the comparative compound was increased.

TEST EXAMPLE 2

A dimethyl formamide solution (1,000 ppm) of Compound (1a-3) was diluted with water to have a predetermined concentration (50, 100 or 200 μM) to prepare a test liquid. In a separate procedure, *Burkholderia glumae* were seeded to an LB culture medium and cultured overnight at 37° C., preparing an broth for infection.

Each test liquid (10 mL) was sprayed onto Korean rice (Milyang 23) raised in a hothouse until the flowering stage. The broth for infection was sprayed onto the rice one hour after the application of the test liquid. After cultivation for seven days, the onset of *Burkholderia glumae* infection on the rice was evaluated.

The evaluation was conducted by picking an ear from each plant, making a total of three ears. In each flower cluster (grain), the percentage of the portion that suffered from the onset of infection (i.e., the portion that turned brown) caused by the toxoflavin produced by *Burkholderia glumae* was visually observed and scored based on the scale shown below. The percentage of the total flower clusters was obtained and scored to indicate the onset of the infection.

Evaluation Criteria

The percentage that suffered from the onset of infection:
Less than 0.1%: 0
Not less than 0.1% and not greater than 20%: 1
Not less than 20% and not greater than 40%: 2
Not less than 40% and not greater than 60%: 3
Not less than 60% and not greater than 80%: 4
Not less than 80% to 100%: 5

In this evaluation, three flower clusters (grains) having the same conditions were prepared, and reproducibility was confirmed by repeating the same evaluation three times. The same evaluation was also conducted as a comparative test except that water was used instead of the test liquid. Further, the same evaluation was conducted to serve as a blank except that water was used instead of both the test liquid and the broth for infection.

Figure 2:
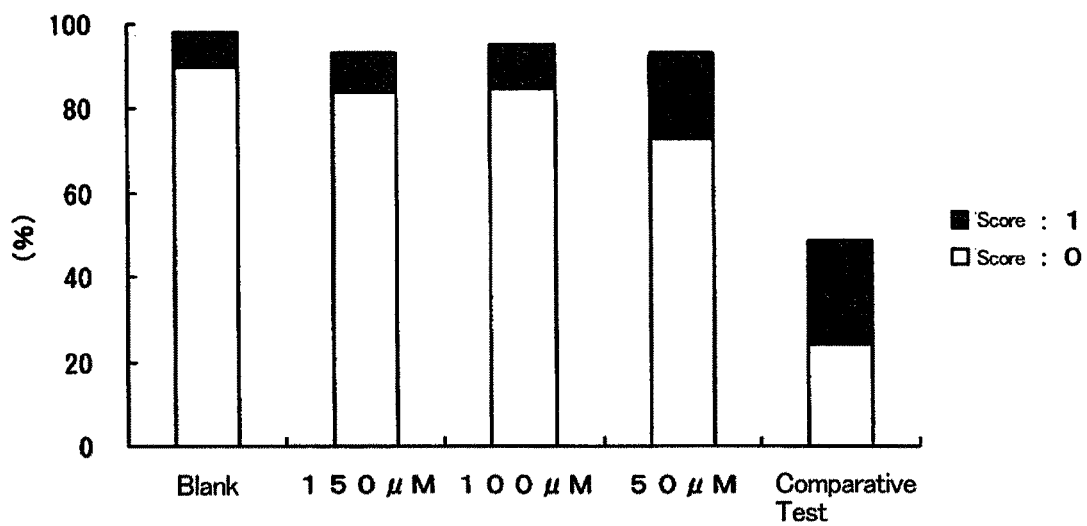

Table 1 shows the results. FIG. 2 shows the results focusing on the scores of 0 and 1.

TABLE 1

| Score | Blank | Compound (1a-3) | | | Comparative Test |
|---|---|---|---|---|---|
| | | 50 μM | 100 μM | 150 μM | |
| 0 | 90% | 73% | 85% | 84% | 24% |
| 1 | 8% | 20% | 10% | 9% | 25% |
| 2 | 2% | 6% | 3% | 4% | 18% |
| 3 | 0% | 1% | 0% | 1% | 19% |
| 4 | 0% | 0% | 1% | 1% | 6% |
| 5 | 0% | 0% | 1% | 1% | 8% |

As is clear from Table 1 and FIG. 2, when the test liquid containing the amide compound of the present invention (1a-3) was sprayed onto rice, the onset of *Burkholderia glumae* was prevented even when the broth for infection containing *Burkholderia glumae* was also sprayed onto the same rice. In contrast, the comparative test wherein the broth for infection containing *Burkholderia glumae* was sprayed onto rice after spraying water, the onset of *Burkholderia glumae* infection was observed in many of the rice samples.

TEST EXAMPLE 3

Figure 3:
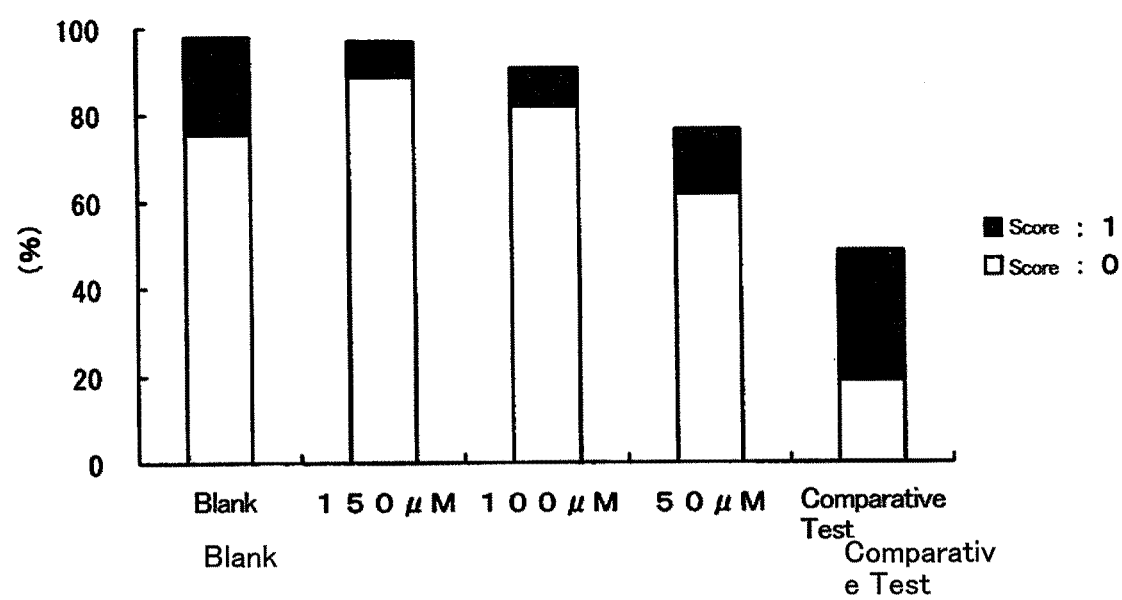

Each test liquid (10 mL) was sprayed onto Korean rice (Milyang 23) raised in a hothouse until the flowering stage. The broth for infection was sprayed onto the rice one hour after the application of the test liquid. After cultivation for seven days, the onset of *Burkholderia glumae* infection on the rice was evaluated in the same manner as in Test Example 2. The same evaluation was conducted as the comparative test in the same manner except that water was used instead of the test liquid. Further, the same evaluation was conducted to serve as a blank using water instead of both the test liquid and the broth for infection. Table 2 shows the results. FIG. 3 shows the results focusing on the scores of 0 and 1.

TABLE 2

| Score | Blank | Compound (1a-3) | | | Comparative Test |
|---|---|---|---|---|---|
| | | 50 μM | 100 μM | 150 μM | |
| 0 | 76% | 62% | 82% | 89% | 19% |
| 1 | 22% | 15% | 9% | 8% | 30% |
| 2 | 2% | 19% | 7% | 1% | 32% |
| 3 | 0% | 2% | 1% | 1% | 8% |
| 4 | 0% | 1% | 1% | 1% | 10% |
| 5 | 0% | 1% | 0% | 0% | 1% |

As is clear from Table 2 and FIG. 3, when the test liquid containing Compound (1a-3) was sprayed onto rice, the onset of *Burkholderia glumae* was prevented in the same manner as in Test Example 2 above, even when the broth for infection containing *Burkholderia glumae* was also sprayed onto the same rice. In contrast, the comparative test wherein the broth for infection containing *Burkholderia glumae* was sprayed onto rice after spraying water, the onset of *Burkholderia glumae* infection was observed in many of the rice samples.

The invention claimed is:

1. An amide compound represented by General Formula (1):

(1)

wherein R is a —CH($R^1$)($R^2$) group, $R^1$ is a hydrogen atom or a hydroxyl group, and $R^2$ is a $C_{1-12}$ alkyl group.

2. The amide compound according to claim 1, wherein R is a —CH($R^1$)($R^2$) group, $R^1$ is a hydrogen atom, and $R^2$ is a $C_{2-10}$ alkyl group in General Formula (1).

3. The amide compound according to claim 1, wherein R is a —CH($R^1$)($R^2$) group, $R^1$ is a hydrogen atom, and $R^2$ is a $C_{4-8}$ alkyl group in General Formula (1).

4. The amide compound according to claim 1, wherein R is a —CH($R^1$)($R^2$) group, $R^1$ is a hydrogen atom, and $R^2$ is an n-hexyl group in General Formula (1).

5. An agricultural or horticultural bacterial infection control agent, comprising an amide compound represented by General Formula (1):

(1)

wherein R is a —CH($R^1$)($R^2$) group, $R^1$ is a hydrogen atom or a hydroxyl group, and $R^2$ is a $C_{1-12}$ alkyl group.

6. The control agent comprising an amide compound according to claim 5, wherein R is a —CH($R^1$)($R^2$) group, $R^1$ is a hydrogen atom, and $R^2$ is a $C_{2-10}$ alkyl group in General Formula (1).

7. The control agent comprising an amide compound according to claim 5, wherein R is a —CH($R^1$)($R^2$) group, $R^1$ is a hydrogen atom, and $R^2$ is a $C_{4-8}$ alkyl group in General Formula (1).

8. The control agent comprising an amide compound according to claim 5, wherein R is a —CH($R^1$)($R^2$) group, $R^1$ is a hydrogen atom, and $R^2$ is an n-hexyl group in General Formula (1).

9. The control agent comprising an amide compound according to claim 5, wherein the bacterial infection is *Burkholderia* infection.

* * * * *